US006469212B1

(12) United States Patent
Prindle, Jr. et al.

(10) Patent No.: US 6,469,212 B1
(45) Date of Patent: Oct. 22, 2002

(54) SEPARATION OF 2,4-TOLUENEDIAMINE FROM AN ISOMERIC MIXTURE OF TOLUENEDIAMINES

(75) Inventors: John C. Prindle, Jr., Baton Rouge; Michael W. Easson, Plaquemine, both of LA (US); James Dee Palmer, Magnolia, AK (US); Jason G. Jones, Baton Rouge, LA (US); Max K. Mortensen, Baton Rouge, LA (US); James E. Boone, Baton Rouge, LA (US)

(73) Assignee: Albemarle Corporation, Richmond, VA (US)

( * ) Notice: Subject to any disclaimer, the term of this patent is extended or adjusted under 35 U.S.C. 154(b) by 0 days.

(21) Appl. No.: 09/531,210

(22) Filed: Mar. 20, 2000

(51) Int. Cl.$^7$ .............................................. C07C 209/00
(52) U.S. Cl. ...................................... 564/424; 564/437
(58) Field of Search ................................. 564/424, 437

(56) References Cited

U.S. PATENT DOCUMENTS

| | | | |
|---|---|---|---|
| 3,960,963 A | 6/1976 | Gavin | 260/582 |
| 4,595,742 A | 6/1986 | Nalepa et al. | 528/64 |
| 4,633,018 A | 12/1986 | Zinnen | 564/424 |
| 4,760,188 A | 7/1988 | Ramken et al. | 564/440 |
| 4,982,002 A | 1/1991 | McKinnie et al. | 564/440 |
| 5,401,867 A | 3/1995 | Sitzmann et al. | 554/211 |

FOREIGN PATENT DOCUMENTS

| | | |
|---|---|---|
| FR | 2566398 | 12/1985 |
| GB | 1320879 | 6/1973 |
| GB | 1481587 | 8/1977 |

OTHER PUBLICATIONS

CA Plus Abstract of French Patent 2,566,398, 1988.
Brochure from Sulzer Chemtech, "Fractional Crystallization–falling film, static, scraped wall", 1991, 18 pages.
Sloan et al., Techniques of Melt Crystallization, Techniques of Chemistry, vol. 19, John Wiley & Sons, 1988, pp. 13–18.
Walas, Stanley M., Phasee Equilibria in Chemical Engineering, Butterworth Publishers, 1985, chapter 8, pp. 397–414.

*Primary Examiner*—Samuel Barts
(74) *Attorney, Agent, or Firm*—Edgar R. Spielman, Jr.

(57) ABSTRACT

A mixture comprised of about 60–85% of 2,4-toluenediamine (2,4-TDA) and about 15–40% of 2,6-toluenediamine (2,6-TDA) is melted, the temperature of the mixture is lowered to a 2,4-TDA nucleation temperature, and the temperature of the mixture is gradually reduced from the nucleation temperature to about 65 to about 70° C. The resultant mixture is in the form of a solids phase enriched in 2,4-TDA, and a novel and useful liquid phase enriched in 2,6-TDA. These phases are separated. Preferably the solids are further purified by "sweating" them and removing the sweated liquid impurities. The sweated liquid can be recycled together with another charge of a mixture comprised of 2,4-TDA and 2,6-TDA. 2,4-TDA can be produced with a purity of 96–99%.

29 Claims, 6 Drawing Sheets

SEPARATION OF 2,4-TOLUENEDIAMINE FROM AN ISOMERIC MIXTURE OF TOLUENEDIAMINES

BACKGROUND

Known methods for producing toluenediamines typically form these products as isomeric mixtures. Close boiling isomeric mixtures are separated by distillation to produce valuable products of which the most common and lowest cost product is a mixture of about 80% 2,4-toluenediamine (2,4-TDA), 19% 2,6-toluenediamine (2,6-TDA), and 1% 2,5-toluenediamine (2,5-TDA). Another chemical route yields mixture of about 65% 2,4-TDA, and about 35% 2,6-TDA. Further separation of these isomers by additional distillation has been shown to be impractical and non-viable financially.

2,4-TDA is useful as an intermediate for the synthesis of 3,5-dimethylthio-2,4-toluenediamine, which is a curative for TDI polyether and TDI polyester prepolymers.

Thus the need has arisen for an effective, commercially-feasible method for separating 2,4-TDA of suitably high purity from an isomeric mixture of toluenediamines, especially a mixture comprising at least 2,4-TDA and 2,6-TDA and in which from about 60 to about 85% of the mixture is 2,4-TDA, and from about 15 to about 40% of the mixture is 2,6-TDA. Such mixtures to be processed may also contain small amounts of 2,5-TDA, e.g., amounts of up to about 1%.

SUMMARY OF THE INVENTION

In the fulfillment of the foregoing need, this invention provides in one of its embodiments a process for separating 2,4-TDA of a purity of at least about 96 wt % from a mixture of toluenediamine isomers comprising at least 2,4-TDA and 2,6-TDA and in which from about 60 to about 85% of the mixture is 2,4-TDA and from about 15 to about 40% of the mixture is 2,6-TDA. The method comprises:

A) melting the isomer mixture, and then lowering the temperature of the mixture to a 2,4-toluenediamine nucleation temperature so that crystals plate out on a cooling surface;

B) gradually reducing the temperature of the mixture from the nucleation temperature to a temperature in the range of about 65 to about 70° C. such that the mixture is in the form of (i) a solids phase enriched in 2,4-toluenediamine, at least a portion of the solids phase being attached to the cooling surface, and (ii) a liquid phase enriched in 2,6-toluenediamine; and C) separating these phases from each other, preferably by draining from the solids attached to the cooling surface, the liquid phase enriched in 2,6-toluenediamine.

Before commencing the gradual reduction in temperature in B), it is preferred to maintain the isomer mixture formed in A) at the nucleation temperature for a period of time sufficient, but not substantially in excess of the time required, for the desired purity of the crystal lattice being formed to be achieved. Typically this period of time is somewhere in the range of about 0.25 to about 3 hours, depending upon the composition of the particular isomer mixture being processed, and the thermal conductivity and roughness of the surface on which the crystallization takes place. Shorter or longer time periods can be employed, however, whenever deemed necessary or desirable, and are within the scope of this invention.

In a preferred embodiment the time period in B) in which the temperature is gradually reduced from the nucleation temperature is in the range of about 6 to about 16 hours.

Another preferred embodiment of this invention is a method which enables maximization of 2,4-toluenediamine purity. This method comprises the following steps conducted seriatim:

a) melting the initial isomer mixture described above, and then lowering the temperature of the mixture to a 2,4-toluenediamine nucleation temperature so that crystals plate out on a cooling surface;

b) maintaining the mixture at the nucleation temperature for a period of time, which typically is in the range of about 0.25 to about 3 hours and preferably is in the range of about 0.75 to about 3 hours, that enables the 2,4-TDA solids remaining after conducting f) hereinafter to reach a purity of at least 96% and preferably of at least 98%;

c) gradually reducing the temperature of the mixture from the nucleation temperature to a temperature in the range of about 65 to about 70° C. such that the mixture is in the form of (i) a solids phase enriched in 2,4-toluenediamine, at least a portion of the solids phase being attached to the cooling surface, and (ii) a liquid phase enriched in 2,6-toluenediamine;

d) separating these phases from each other, preferably by draining from the solids attached to the cooling surface, the liquid phase enriched in 2,6-toluenediamine;

e) heating slowly at least a portion of the solids phase remaining after the separation of d) so that impurities "sweat" from the solids as liquids, and f) separating these liquids or "sweat" from the solids essentially as soon as these liquids or "sweat" are being formed, preferably by continuously draining the liquids or "sweat" away from the solids as soon they are formed.

Another step which is usually, but not necessarily, performed is to recover the solids remaining after completion of f). Preferably such recovery is accomplished by melting the solids remaining in the apparatus in which the overall operation is conducted (typically a melt crystallizer), and draining the melted solids from the apparatus. Instead of recovering these purified solids, it may be possible, depending upon the design of the apparatus, to react the solids while in the apparatus with a suitable reactant to form another desired product in situ, such as 3,5-di(methylthio)-2,4-toluenediamine, which is then recovered from the apparatus.

Typically the purified solids remaining after completion of f) contain about 96–99% 2,4-TDA, up to about 1% 2,5-TDA, with the balance, if any, being 2,6-TDA. Optimally, the composition of the "sweat" is close to that of the initial feed to the process, e.g., ca. 80% 2,4-TDA and ca. 20% 2,6-TDA, or ca. 65% 2,4-TDA and ca. 35% 2,6-TDA.

Typically the liquid phase enriched in 2,6-toluenediamine formed in c) comprises about 36 to about 49% of 2,6-toluenediamine, optionally, up to about 1% of 2,5-toluenediamine, and wherein essentially all of the balance to 100% is 2,4-toluenediamine. In preferred compositions about 45 to about 49% of the composition is 2,6-toluenediamine. Such novel and useful compositions constitute still further embodiments of this invention.

If desired, the separated "sweat" is recovered and recycled to a) together with another charge of a mixture of toluenediamine isomers comprising at least 2,4-TDA and 2,6-TDA.

Among the highly advantageous features of this invention is that a pair of highly useful products can be produced concurrently by the present process technology. First, the process enables the recovery in good yield of 2,4-TDA with a purity of 96–99%. So far as is presently known, no prior, commercially-practicable process has the capability of accomplishing this without substantially greater capital expenditure. Secondly, as described more fully in commonly-owned copending Application Ser. No. 09/528,837, filed Mar. 20, 2000, the liquid phase enriched in 2,6-toluenediamine formed in the present process, has been found to be an especially desirable starting material for the preparation of mixtures comprised of 3,5-dimethylthio-2,6-toluenediamine and 3,5-dimethylthio-2,4-toluenediamine. These latter mixtures when used as curatives with isocyanate prepolymers enable formation of polyurethane polymers having very desirable thermo-mechanical properties.

Still other embodiments and features of this invention will become still further apparent from the ensuing description and appended claims.

FURTHER DETAILED DESCRIPTION

Figure 1:
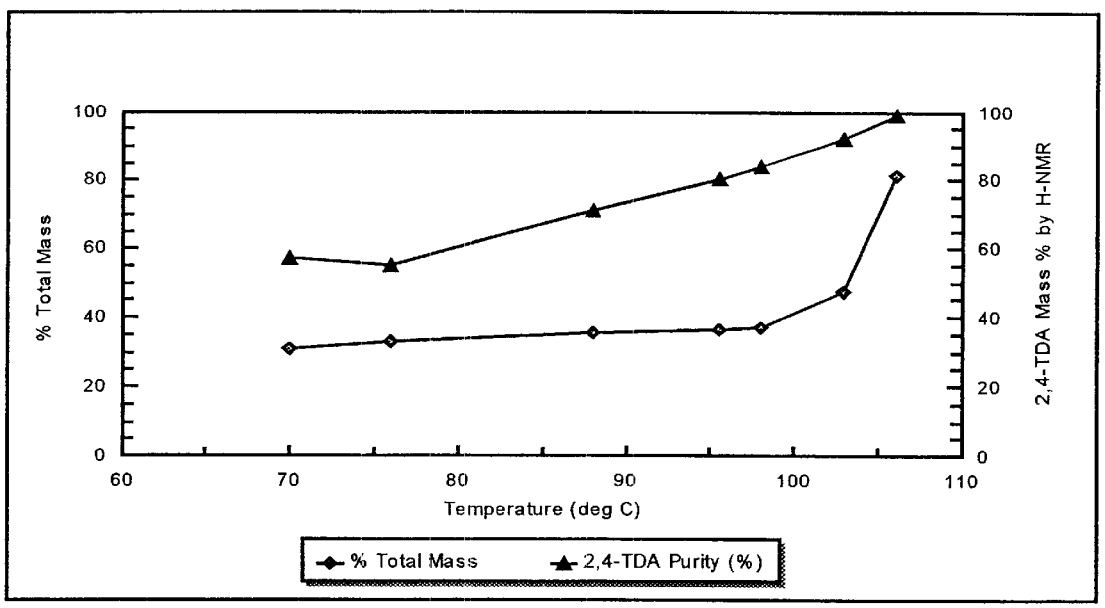
FIGS. 1–5 are graphical presentations of the respective results obtained in Examples 1–5 hereof.
Figure 2:
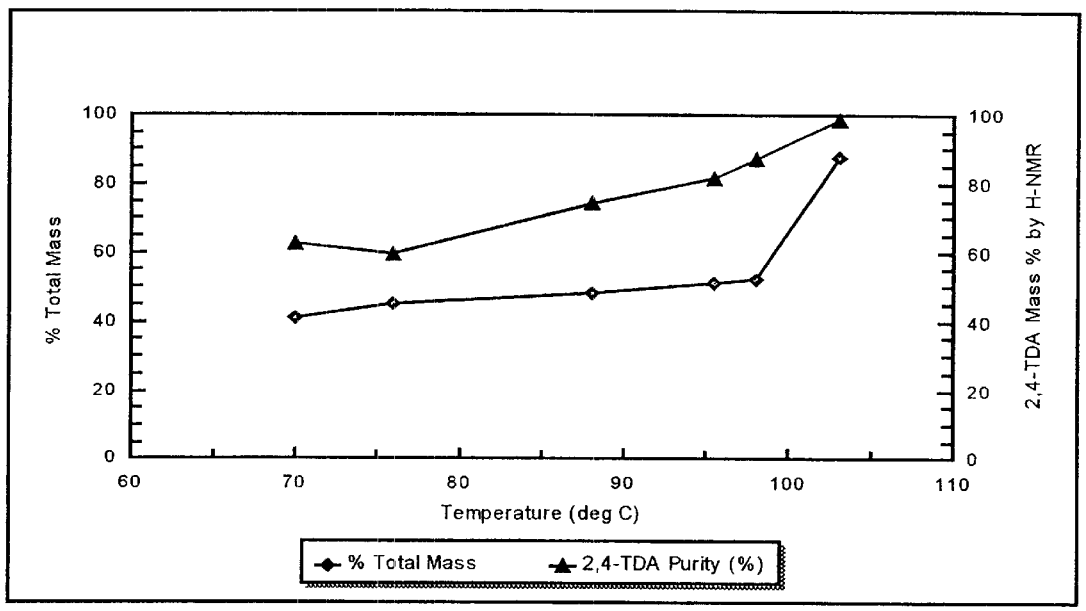
Figure 3:
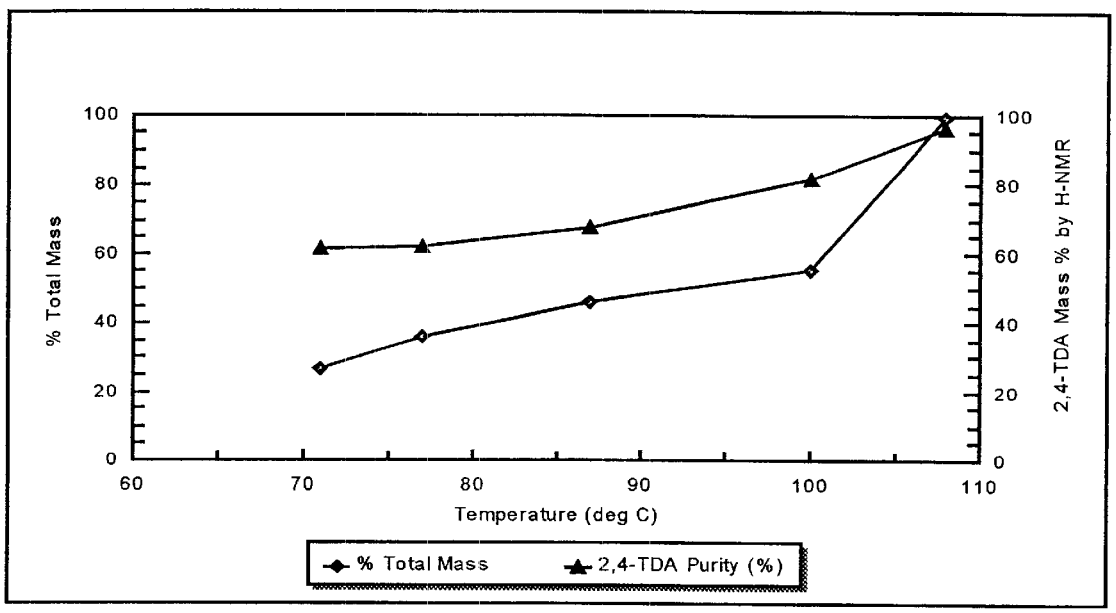
Figure 4:
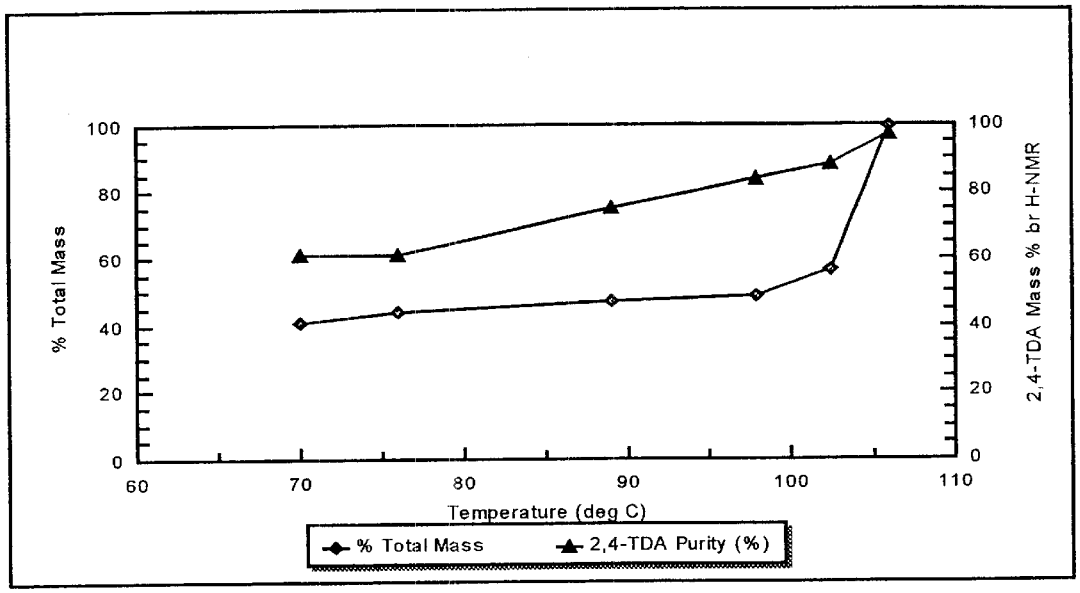
Figure 5:
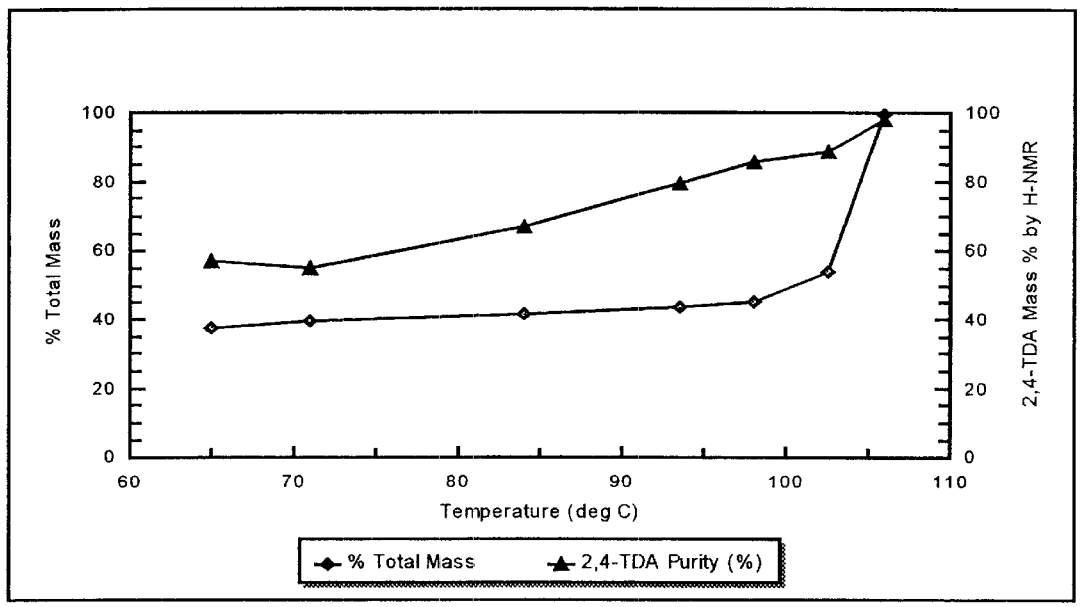

For ease of reference, the abbreviation m-TDA refers to a mixture of toluenediamine isomers which includes at least 2,4-TDA and 2,6-TDA.

This invention is applicable to the recovery of 2,4-TDA from mixtures containing at least one other TDA isomer. It is desirable that 2,4-TDA constitute at least about 60% of the mixture subjected to the process of this invention. A preferred isomeric mixture for use as a raw material in the process is commercially available from Air Products and Chemicals, Inc., and is composed of 79–81% of 2,4-TDA, 19–21% of 2,6-TDA, and a maximum of 1.0% of 2,5-TDA. Another useful product for use as the raw material for the present process is composed of about 65% 2,4-TDA and about 35% 2,6-TDA. The latter product is available primarily in Europe at a relatively high price.

A feature of this invention is that it makes possible in preferred embodiments the production of two very desirable end products. More particularly, one such product is 2,4-TDA of a purity of at least about 96%, and preferably of at least about 98%. The co-product is a novel TDA mixture which comprises about 36 to about 49% of 2,6-toluenediamine, optionally up to about 1% of 2,5-toluenediamine, and with essentially all of the balance to 100% being 2,4-toluenediamine. Preferred co-products are those in which about 45 to about 49% of the mixture is 2,6-toluenediamine. As noted above, 2,4-TDA is particularly useful as an intermediate for the synthesis of 3,5-di(methylthio)-2,4-toluenediamine. Suitable process conditions that can be used for producing 3,5-di(methylthio)-2,4-toluenediamine from the high purity 2,4-TDA products made available by this invention are set forth in U.S. Pat. No. 4,760,188. 3,5-Di(methylthio)-2,4-toluenediamine products produced from high purity 2,4-TDA products made available by this invention have slow polyurethane gel/cure times which are advantageous for certain types of molding operations as described more fully in commonly-owned copending Application Ser. No. 09/528,530, filed Mar. 20, 2000, abn. The 2,6-TDA enriched co-product mixtures are also useful in forming di(methylthio)toluenediamine mixtures that can give faster gel/cure times and greater structural stability to polyurethane. In this case, it is desirable to utilize the catalytic processing described in U.S. Pat. No. 4,982,002 for converting the 2,6-TDA enriched co-product mixtures of this invention into such di(methylthio)toluenediamine mixtures.

Various melt crystallizers suitable for use in the practice of this invention are available commercially. Such crystallizers include continuous crystallizers and falling-film crystallizers. One dynamic crystallizer unit which may be used is a falling-film crystallizer manufactured by Sulzer-Chem Tech. However, if desired, apparatus can be specifically designed and constructed for performing the process of this invention. For further details concerning the design and construction of melt crystallizers, see Gilbert J. Sloan and Andrew R. McGhie, Techniques of Melt Crystallization, John Wiley & Sons, copyright 1988, especially pages 399–421. This entire book is incorporated herein by reference as if fully set forth herein.

The nucleation temperature of 2,4-toluenediamine is in the vicinity of about 90° C. although the nature and content of impurities in the mixture being processed can cause some variation in the nucleation temperature.

Of primary importance in melt crystallization is the time dedicated to the formation of the crystalline lattice. It has been reported that organic crystals typically grow isothermally at a rate of less than 3×E-4 cm/s (Sloan, 1988). This crystallization rate is regulated by the liberation of the heats of fusion at the solid/liquid interface and eventually ceases when the thickness of the crystalline lattice prohibits further crystallization. These newly-formed crystals act as an insulator, resulting in an equilibrium at the solid/liquid interface. To form additional crystals the temperature must be lowered, creating a thermal driving force, and allowing once more for the liberation of the heats of fusion generated by the formation of new crystals.

It is not desirable to remain at a given temperature after the crystalline lattice of the desired purity and thickness has formed. Yet it is essential that the appropriate time be dedicated at the given temperature in order for a crystalline lattice of the desired purity to be formed before lowering the temperature.

As noted above, step b) involves maintaining the mixture from a) at the nucleation temperature that will enable the 2,4-TDA solids remaining after conducting step f) to reach a purity of at least 96% and preferably of at least 98%. Typically this involves holding the mixture from a) at the nucleation temperature for a period of time in the range of about 0.25 to about 3 hours and preferably is in the range of about 0.75 to about 3 hours. During such periods of time increased crystalline thickness tends to occur in the crystalline lattice of the crystals that have been formed on the cooling surface.

In any situation where the optimal operating conditions for any given feed material and apparatus have not been previously established, it is desirable to perform a few pilot operations in order to develop a set of optimal operating conditions for the particular raw material and apparatus being used.

Of the five experiments constituting Examples 1–5 hereinafter, three utilized a twelve to fourteen hour crystallization period while the remaining two employed an 8.0 and 10.6 hour crystallization period.

Whenever the crystallization characteristics of a particular m-TDA raw material have not already been established, it is desirable to perform preliminary differential scanning calorimetry (DSC) tests using suitable proportions of different mixtures made from pure 2,4-TDA and 2,6-TDA. The purpose of this test is to determine the upper temperature limit wherein the initial nucleation of 2,4-TDA crystals occurs. For convenience, this temperature is sometimes referred herein as the 2,4-toluenediamine nucleation temperature. In the case of a mixture composed of 79–81% of 2,4-TDA, 19–21% of 2,6-TDA, and a maximum of 1.0% of 2,5-TDA, the onset of nucleation was indicated by DSC to be approximately 90° C. Thus for mixtures within this particular composition range, typically the 2,4-toluenediamine nucleation temperature used is approximately 90±2°.

If the lowest temperature at which a mixture of 2,4-TDA and 2,6-TDA can coexist as a liquid without forming a solid is not known, it is desirable to perform additional DSC tests on reagent grade samples of 2,4-TDA 2,6-TDA to determine the heats of fusion of these materials. This data is used to generate a liquid/solid phase diagram using the Shroder Equation. Phase diagram information is used in calculating the lowest temperature and lowest 2,4-TDA content at which the two TDA isomers can coexist as a liquid. Phase diagrams may also be useful in estimating the theoretical yield and operating temperature parameters.

Figure 6:
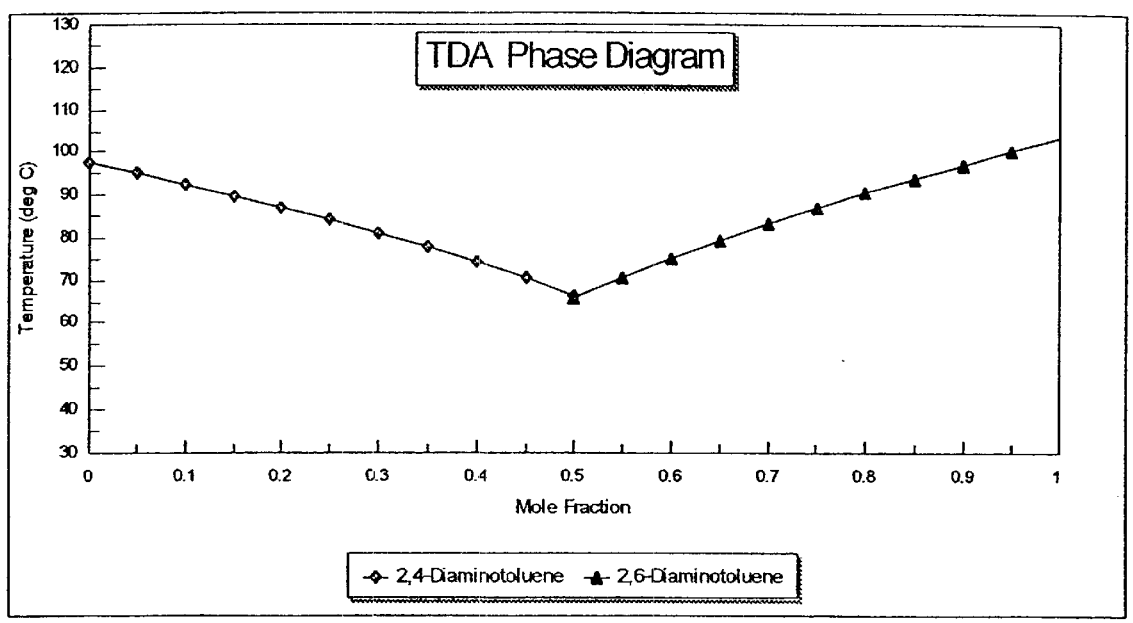
FIG. 6 is a phase diagram for 2,4-toluenediamine and 2,6-toluenediamine.

The lowest temperature and 2,4-TDA content at which the two TDA isomers can coexist as a liquid is known as the eutectic point. Based upon the phase diagram for 2,4-TDA and 2,6-TDA determined in this manner and presented in FIG. 6, the eutectic temperature is 68° C. and the corresponding composition is 50% 2,4-TDA and 50% 2,6-TDA. Theoretical yield was calculated to be 60%, and the operating temperature parameter ranged from 68° C. to 99° C. The operating temperature parameter range is the cooling curve along which essentially pure 2,4-TDA can be crystallized.

It is important to note that this phase diagram was generated using the assumption of ideal liquid phase behavior. Since even mixtures of isomers have been reported to exhibit non-ideal behavior (Walas, 1985), some deviations from the above eutectic composition and temperature are to be expected. These values are thus used to initially estimate the 2,4-TDA yield and lower limit for crystallization temperature.

To produce the highest purity 2,4-TDA, once the crystallization of the 2,4-TDA has been completed, the crystals are preferably "sweated" of 2,5-TDA and 2,6-TDA impurities. This is accomplished by slowly raising the temperature of the melt crystallizer, causing or enabling the liquid impurities to promptly separate and drain away from the solids at least under the influence of gravity, and optionally with the aid of a low pressure nitrogen purge. If the crystallization has proceeded at optimal rates, the 2,4-TDA crystals will have formed to the exclusion of the undesirable isomeric impurities. The task of melting out the impurities then becomes easier, since the contaminants are not trapped within the crystalline lattice.

In any case where the ramp rate for sweating the enriched 2,4-TDA product made from a particular raw material mixture of TDA isomers which includes 2,4-TDA has not already been established, it is desirable to perform preliminary small-scale experiments prior to larger-scale operation. The purpose of such tests is to determine or at least estimate a suitable rate at which the temperature of the crystallized 2,4-TDA should be increased during the sweating step. Typically rates in the range of about 0.1 to about 0.2° C. per minute are suitable for sweating an 80/20 mix of 2,4/2,6-TDA at the scale of operation and geometry of apparatus described in the ensuing Examples.

Generally speaking, the rate at which the temperature is decreased (ramped downwardly) from the temperature of the initial melt to the 2,4-toluenediamine nucleation temperature, and if the sweating operation is used, the rate at which the temperature of the crystallized enriched 2,4-TDA solids is increased during the sweating operation are preferably uniform or substantially uniform. In other words, preferably the temperature is lowered or raised, as the case may be, either at (i) a constant or an essentially constant linear rate, or (ii) at a constant or an essentially constant stepwise rate. Variations in or from any such rates that make no material difference in the results obtained are within the ambit of this invention. However wide fluctuations in temperature during the temperature ramping that adversely affect the results obtained should be avoided.

It is desirable to suitably regulate the crystallization, sweating, and purging times to avoid, or at least minimize, operational difficulties that may arise depending upon the scale of operation, the design of the particular melt crystallizer being used, and the composition of the starting TDA mixture to be processed. Generally speaking, use of longer crystallization times tends to avoid excessive localized crystal buildup which may possibly cause pluggage problems. Subject to variations necessitated by the scale of the operation, the design of the melt crystallizer, and the composition of the starting TDA mixture, crystallization times in the range of about 6 to about 16 hours are preferred. Conversely, shorter sweating and inert gas purging times generally tend to avoid excessive product losses due to excessive product sublimation. Again subject to variations necessitated by the scale of the operation, the design of the melt crystallizer, and the composition of the starting TDA mixture, purging times in the range of about 3 to about 5 hours, and sweating times in the range of about 3 to about 5 hours are preferred. It is to be understood, however, that departures from one or more of these ranges are permissible and are within the scope of this invention whenever such departures are deemed necessary or advisable under any given set of circumstances.

The following Examples illustrate the practice of this invention. However these Examples are not intended to limit, and should not be construed as limiting, the scope of this invention to the particulars described therein. Each Example utilizes the optional, but preferred, sweating operation in order to further purify the 2,4-TDA.

The melt crystallizer used in the Examples is a jacketed, glass cylinder, 35 inches in length and 4 inches in diameter. The lower end of the cylinder curves into a narrow ½ inch tube which is governed by a ground glass stopcock. The upper end is flanged and supports a 4-inch glass head with a 24/40 ground glass fitting in the center of the head. Inserted in the fitting is a jacketed glass coil through which a low pressure nitrogen gas may flow. Both the upper jacketed coil and the lower jacketed cylinder are connected in series by insulated copper tubing through which heat transfer fluid flows. This heat transfer fluid is regulated by a computer-controlled bath which can be programmed by the operator.

Following is a description of the general procedure used in conducting the operations described in the Examples. The specific details for each such operation are set forth in the respective Examples.

Approximately two to five kilograms of crushed TDA composed of 79–81% of 2,4-TDA, 19–21% of 2,6-TDA, and a maximum of 1.0% of 2,5-TDA (Air Products and Chemicals, Inc.) was loaded into the melt crystallizer and melted at 120° C. The temperature was then lowered to the onset of the nucleation point at 90° C. and held there from one to three hours. The temperature was then ramped downwardly to 70° C., except in Example 5 in which the temperature was ramped downwardly to 65° C. The time of this ramping varied from Example to Example in the range of 7 to 14 hours. With a nitrogen purge applied, the temperature was then ramped upwardly from 70° C. (or 65° C.) to 106° C. over six to seventeen hours and the isomeric impurities were removed. The final purified 2,4-TDA material was melted at 120° C., drained from the melt crystallizer, and analyzed for purity. Each experimental cycle lasted approximately twenty-four hours. Samples of the sweat material were continually collected and weighed at 2–15° C. intervals. These samples were then analyzed by H-NMR for 2,4-TDA, 2,5-TDA, and 2,6-TDA mass percentages. The operating parameters for each run are given in the following Examples. Table 1 provides additional details of, and summarizes results obtained in, the respective runs. Table 2 summarizes the data obtained during the sweating operation. The principal results of each Example are depicted graphically in FIGS. 1–5, respectively.

EXAMPLE 1

Crystallization Parameters

1) Melt temperature, 120° C.
2) Downward temperature ramp, 120 to 90° C. initiated immediately after reaching melt temperature
3) Hold at 90° C. for three hours
4) Reduce from 90 to 70 ° C. over 14 hours Sweat Parameters 1) Nitrogen purge applied
2) Hold at 70° C. for 7 hours
3) Idled at 70° C. over a weekend after draining mother liquor
4) Power failure in lab (4:46 a.m. on Monday); temperature dropped to 50.7° C.
5) Power restored (10:12 a.m. on Monday); temperature restored to 70° C. immediately
6) Programmed slow sweat at upward ramp rate of 70 to 106° C. in 9 hours (1° C./15 min)
7) Collected samples during upward ramp of 70 to 106° C.
8) Nitrogen purge discontinued
9) Melted and drained final 2,4-TDA product from melt crystallizer at 106° C.

EXAMPLE 2

Crystallization Parameters

1) Melt temperature, 130° C.
2) Downward temperature ramp, 130 to 90° C. initiated immediately after reaching melt temperature
3) Hold at 90° C. for one hour
4) Reduce from 90 to 70° C. over 7 hours Sweat Parameters 1) Nitrogen purge applied
2) Hold at 70° C. for 5.5 hours
3) Programmed slow sweat at upward ramp rate of 70 to 106° C. in 9 hours (1° C/15 min)
4) Collected samples during upward ramp of 70 to 106° C.
5) Nitrogen purge discontinued
6) Melted and drained final 2,4-TDA product from melt crystallizer at 106° C.

EXAMPLE 3

Crystallization Parameters

1) Melt temperature, 130° C.
2) Downward temperature ramp, 130 to 90° C. initiated immediately after reaching melt temperature
3) Hold at 90° C. for one hour
4) Reduce from 90 to 70° C. over 7 hours
5) Hold at 70° C. for 2 hours, 37 minutes Sweat Parameters 1) Nitrogen purge applied
2) Hold at 70° C. for 36 minutes
3) Ramped immediately to 72° C., and hold there for 2 hours, 57 minutes
4) Programmed fast sweat at upward ramp rate of 72 to 108° C. in 4 hours (2° C./15 min)
4) Collected samples during upward ramp of 72 to 108° C.
5) Nitrogen purge discontinued
6) Melted and drained final 2,4-TDA product from melt crystallizer at 130° C.

EXAMPLE 4

Crystallization Parameters

1) Melt temperature, 123° C.
2) Downward temperature ramp, 123 to 90° C. initiated immediately after reaching melt temperature
3) Hold at 90° C. for one hour
4) Reduce from 90 to 70° C. over 14 hours Sweat Parameters 1) Nitrogen purge applied
2) Hold at 70° C. for 1 hour, 35 minutes
3) Programmed fast sweat at upward ramp rate of 70 to 106° C. in 4.5 hours (2° C/15 min)
4) Collected samples during upward ramp of 70 to 106° C.
5) Nitrogen purge discontinued
6) Melted and drained final 2,4-TDA product from melt crystallizer at 125° C.

EXAMPLE 5

Crystallization Parameters

1) Melt temperature, 125° C.
2) Downward temperature ramp, 125 to 90° C. initiated immediately after reaching melt temperature
3) Hold at 90° C. for one hour
4) Reduce from 90 to 65° C. over 14 hours Sweat Parameters 1) Nitrogen purge applied
2) Hold at 65° C. for 1 hour, 54 minutes
3) Programmed fast sweat at upward ramp rate of 65 to 106° C. in 5 hours, 7 minutes (2° C./15 min)
4) Collected samples during upward ramp of 65 to 106° C.
5) Nitrogen purge discontinued
6) Melted and drained final 2,4-TDA product from melt crystallizer at 125° C.

TABLE 1

|  | Example 1 | Example 2 | Example 3 | Example 4 | Example 5 |
| --- | --- | --- | --- | --- | --- |
| Starting Weight (g) | 2346 | 3490 | 4152 | 3826 | 3252 |
| Crystalline Surface Area (cm²) | 949.8 | 1413.0 | 1681.0 | 1549.0 | 1316.6 |
| (ft²) | 1.022 | 1.521 | 1.809 | 1.667 | 1.417 |
| Crystal Formation Time (Hrs) | 17 | 8 | 10.6 | 15 | 15 |

TABLE 1-continued

|  | Example 1 | Example 2 | Example 3 | Example 4 | Example 5 |
|---|---|---|---|---|---|
| Crystal Sweat Time (Hrs) | 16 | 14.5 | 7.5 | 7 | 7 |
| Total Sweat Mass (g), | 1108 | 2048 | 2292 | 2154 | 1750 |
| Percent (%) | 47.2 | 58.7 | 55.2 | 56.3 | 53.8 |
| Sublimation Loss (g), | 443.3 | 212 | 20 | 16 | 18 |
| Percent (%) | 18.9 | 6.1 | 0.48 | 0.42 | 0.55 |
| Final 2,4-TDA Product Weight (g), | 794.7 | 1230 | 1840 | 1656 | 1484 |
| Percent of Theory (%), | 56.5 | 58.7 | 73.9 | 72.1 | 76.1 |
| Actual (%) | 33.9 | 35.2 | 44.3 | 43.3 | 45.6 |
| Final 2,4-TDA Product Purity (%) | 99 | 98.4 | 96.2 | 97.4 | 98.1 |

Note:
Crystallization area per gram of starting material = 0.4049 cm$^2$/g
Crystallization area per pound of starting material = 0.1977 ft$^2$/b

TABLE 2

| Temp ° C. | Sweat Mass (g) | Sweat Loss (%) | 2,4-TDA (%) | 2,5-TDA (%) | 2,6-TDA (%) |
|---|---|---|---|---|---|
| Example 1 | | | | | |
| 70 | 719.3 | 30.7 | 57.3 | 1.4 | 41.4 |
| 70–82.4 | 59.0 | 2.5 | 55.2 | 1.0 | 43.9 |
| 82.4–94 | 51.3 | 2.2 | 70.8 | 0.7 | 28.5 |
| 94–97 | 21.9 | 0.9 | 80.4 | 0.4 | 19.2 |
| 97–99 | 22.0 | 0.9 | 83.6 | 0.4 | 16.0 |
| 99–106 | 234.7 | 10.0 | 92.3 | 0.2 | 7.5 |
| 106 | 794.7 | 33.9 | 99.0 | 0.0 | 1.0 |
| Example 2 | | | | | |
| 70 | 1422 | 40.7 | 62.7 | 1.0 | 36.4 |
| 70–81.2 | 144 | 4.1 | 59.6 | 1.0 | 39.4 |
| 81.2–91.8 | 114 | 3.3 | 74.1 | 0.6 | 27.9 |
| 91.8–97.8 | 106 | 3.0 | 81.5 | 0.5 | 18.0 |
| 97.8–99 | 44 | 1.3 | 87.0 | 0.3 | 12.7 |
| 99–106 | 218 | 6.25 | —* | —* | —* |
| 106 | 1230 | 35.2 | 98.4 | 0.0 | 1.6 |
| Example 3 | | | | | |
| 70–72 | 1108 | 26.7 | 61.2 | 1.1 | 37.6 |
| 72–81.7 | 388 | 9.3 | 62.0 | 1.1 | 37.0 |
| 81.7–92.7 | 414 | 10.0 | 67.4 | 0.9 | 31.7 |
| 92.7–108 | 382 | 9.2 | 81.8 | 0.4 | 17.6 |
| 108 | 1840 | 44.3 | 96.2 | 0.0 | 3.8 |
| Example 4 | | | | | |
| 70 | 1566 | 40.9 | 61.0 | 1.2 | 37.8 |
| 70–82.5 | 108 | 2.8 | 60.9 | 1.0 | 38.1 |
| 82.5–97.0 | 134 | 3.5 | 75.1 | 0.6 | 24.2 |
| 97.0–99 | 60 | 1.6 | 83.7 | 0.4 | 15.8 |
| 99–106 | 286 | 7.5 | 88.0 | 0.3 | 11.7 |
| 106 | 1656 | 43.3 | 97.4 | 0.0 | 2.6 |
| Example 5 | | | | | |
| 65 | 1210 | 37.2 | 56.8 | 1.3 | 41.9 |
| 65–77.5 | 74 | 2.3 | 55.1 | 1.2 | 43.7 |
| 77.5–90 | 60 | 1.9 | 66.9 | 1.0 | 32.1 |
| 90–97 | 72 | 2.2 | 79.4 | 0.6 | 20.1 |
| 97–99 | 46 | 1.4 | 85.7 | 0.4 | 13.9 |
| 99–106 | 288 | 8.9 | 88.6 | 0.3 | 11.1 |
| 106 | 1484 | 45.6 | 98.1 | 0.0 | 1.9 |

As can be seen from Examples 1–4, those operations were performed using a crystallization temperature range from 90° C. to 70° C. This range was selected on the basis of preliminary DSC analyses and the resultant phase diagram depicted in FIG. 6. Under the crystallization conditions used in Examples 1–4 and assuming ideal behavior, the composition of the eutectic mixture should have closely compared to the predicted theoretical composition of 50% 2,4-TDA and 50% 2,6-TDA. H-NMR results showed, however, that the mixtures did not exhibit ideal behavior. The eutectic compositions of Examples 1–4 were closer to 60% 2,4-TDA and 40% 2,6-TDA. More particularly, the compositions formed in Examples 1–4 which came closest in composition to the theoretical eutectic composition were as follows:

Example 1-57.3% 2,4-TDA, 41.4% 2,6-TDA, and 1.4% 2,5-TDA

Example 2-62.7% 2,4-TDA, 36.4% 2,6-TDA, and 1.0% 2,5-TDA

Example 3-61.2% 2,4-TDA, 37.6% 2,6-TDA, and 1.1% 2,5-TDA

Example 4-61.0% 2,4-TDA, 37.8% 2,6-TDA, and 1.2% 2,5-TDA

In Example 5 wherein the crystallization temperature range used was 90 down to 65° C., the H-NMR results for the composition approximating the eutectic composition indicated that the composition approximating the eutectic composition contained 56.8% 2,4-TDA, 41.9% 2,6-TDA, and 1.3% 2,5-TDA. In each of Examples 1–5, the 2,4-TDA product after the sweating operation was of high purity (96–99%). These results illustrate the fact that this invention makes it possible to provide in one operation both a high purity 2,4-TDA product as well as a composition approximating the eutectic composition within a range of product composition, by suitable control of the conditions employed in the overall process wherein a sweating operation is included.

From the above Examples it can be seen that difference in crystallization time can be of significance on the formation of crystals in the melt crystallizer. In Examples 2 and 3 where the shortest crystallization times were used (8 hours and 10.6 hours, respectively), crystals tended to form as one solid mass in the center of the melt crystallizer used, causing significant clogging problems when an effort was made to sweat off the impurities. These clogging problems meant a longer period of time was spent at the eutectic temperature trying to collect the impurities and clear the clogs.

In contrast, in Examples 1, 4 and 5 where the longest crystallization times were used, (17 hours, 15 hours, and 15 hours, respectively), the crystals formed in large, spectacular, brown feather patterns along the surface area of the melt crystallizer. The crystals extended inward approximately one inch, with the remaining two-inch diameter space filled with impurity-enriched, liquid TDA material. The removal of impurities in these runs was much easier than in those with short crystallization times. Blockage, while not totally absent, was reduced significantly and the application of a 15-watt heat gun was occasional, instead of often. Thus, while the shorter crystallization time did not have a significant impact on the overall yield and purity, it did have an effect on the ease with which the process operation could be conducted in the particular melt crystallizer employed.

To minimize, sublimation losses during the operation, it is desirable to minimize nitrogen (or other inert gas) purge times used in removing impurities. This is illustrated by comparing Examples 1 and 2 with Examples 3–5. By reducing the purging times from 17 and 14.5 hours to 7.0 to 7.5 hours, sublimation losses were significantly reduced. Accordingly, for best results at least when using a starting mixture such as employed in the Examples, it is desirable to avoid use of lengthy sweat and purge times.

The results of Examples 1–5 show that a single-stage melt crystallizer is adequate on a commercial scale for separating an isomeric mixture of TDA of the type utilized therein into a >95% pure 2,4-TDA product. Because of the scale of this work, the numerical value of the heat-transfer area per mass of processed material reported here (i.e., 0.2 ft$^2$/lb) is deemed adequate with a twenty-four hour cycle time.

It will be understood that as used herein, including the ensuing claims, terms such as "the", "said", and "such" with reference to a substance to be acted upon, do not constitute absolutes. For example, when separating or draining "the", "said", or "such" liquid from "the", "said", or "such" solid does not mean that every last speck of liquid must be separated or drained from the solid. Likewise, heating "the", "said", or "such" material from a prior step does not mean that every last speck of the material from the prior step must be heated. Instead, in the first example given, the amount of the material being separated or drained relative to the original amount available would be as much as would be reasonable when one of ordinary skill in the art would conduct such a separation or draining given the particular circumstances involved in conducting such operation. Similarly, in the second example given, one might elect to withdraw a portion of the material from the prior step for analysis or for some other reason or purpose, and therefore heat less than the amount of material originally available for heating, even though in most cases one would probably heat all such material that is available from the prior step. Thus terms such as "the", "said", "such" and others of similar import, especially to the extent they may appear in the ensuing claims, should be read and understood with ordinary common sense rather than with legalistic pretentiousness.

This invention is susceptible to considerable variation in its practice. Therefore the fore-going description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A process for separating 2,4-toluenediamine of a purity of at least about 96 wt % from a mixture of toluenediamine isomers comprising at least 2,4-toluenediamine and 2,6-toluenediamine and in which from about 60 to about 85 wt % of the mixture is 2,4-toluenediamine and from about 15 to about 40 wt % of the mixture is 2,6-toluenediamine, said method comprising:
   A) melting the isomer mixture, and then lowering the temperature of the mixture to a 2,4-toluenediamine nucleation temperature;
   B) gradually reducing the temperature of the mixture from the nucleation temperature to a temperature in the range of about 65 to about 70° C. such that the mixture is in the form of a solids phase enriched in 2,4-toluenediamine, and a liquid phase enriched in 2,6-toluenediamine; and
   C) separating these phases from each other.

2. A process of claim 1 wherein, before commencing said gradual reduction in temperature in b), the isomer mixture formed in a) is maintained at the nucleation temperature for a period of time sufficient for a crystal lattice to be formed.

3. A process of claim 1 wherein the isomer mixture formed in A) is maintained at the nucleation temperature for a period of time in the range of about 0.25 to about 3 hours, before commencing said gradual reduction in temperature.

4. A process of claim 1 wherein, in B), the time period in which the temperature is gradually reduced is in the range of about 6 to about 16 hours.

5. A process of claim 1 wherein to effect the separation in C) liquid phase is drained away from said solids phase.

6. A process of claim 1 wherein said liquid phase enriched in 2,6-toluenediamine comprises about 36 to about 49 wt % of 2,6-toluenediamine, about 51 to about 63 wt % of 2,4-toluenediamine, and up to about 1 wt % of 2,5-toluenediamine.

7. A process of claim 1 further comprising:
   D) heating slowly solids phase remaining after the separation of C) so that impurities drip off or "sweat" as liquids, and
   E) separating such liquids or "sweat" from the purified solids.

8. A process of claim 7 further comprising recovering purified solids remaining after the separation in E).

9. A process of claim 8 wherein said purified solids contain in the range of about 96 to about 99 wt % of 2,4-toluenediamine, up to about 1 wt % of 2,5-toluenediamine, with the balance, if any, consisting essentially of 2,6-toluenediamine.

10. A process of claim 8 wherein said purified solids are recovered by melting them, and draining and collecting such melted solids.

11. A process of claim 7 wherein the separation in E) is effected by draining away liquid from the solids.

12. A process of claim 11 further comprising recovering purified solids remaining after the draining.

13. A process of claim 12 wherein said purified solids are recovered by melting them, and draining and collecting such melted solids.

14. A process of claim 13 wherein collected, melted solids are re-solidified by temperature reduction, and wherein the resultant solid(s) contain(s) in the range of about 96 to about 99 wt % of 2,4-toluenediamine, up to about 1 wt % of 2,5-toluenediamine, with the balance, if any, consisting essentially of 2,6-toluenediamine.

15. A process for separating 2,4-toluenediamine from a mixture of toluenediamine isomers comprising at least 2,4-toluenediamine and 2,6-toluenediamine and in which from about 60 to about 85 wt % of the mixture is 2,4-toluenediamine and from about 15 to about 40 wt % of the mixture is 2,6-toluenediamine, said method comprising:
   a) melting said mixture, and then lowering the temperature of the mixture to a 2,4-toluenediamine nucleation temperature;
   b) gradually reducing the temperature of the mixture from the nucleation temperature to a temperature in the range of about 65 to about 70° C. such that the mixture is in the form of a solids phase enriched in 2,4-toluenediamine, and a liquid phase enriched in 2,6-toluenediamine;
   c) separating the liquid phase from the solids;
   d) gradually raising the temperature of the solids to a temperature in the range of about 65 to about 106° C., such that additional liquid is formed; and
   e) separating from the solids additional liquid formed in d) such that the solids are further enriched in 2,4-toluenediamine.

16. A process of claim 15 wherein, before commencing said gradual reduction in temperature, the isomer mixture formed in a) is maintained at the nucleation temperature for a period of time sufficient for increasing the thickness of the crystal lattice being formed at said temperature.

17. A process of claim 15 wherein the isomer mixture formed in a) is maintained at the nucleation temperature for a period of time in the range of about 0.25 to about 3 hours, before commencing said gradual reduction in temperature.

18. A process of claim 15 wherein the isomer mixture formed in a) is maintained at the nucleation temperature for a period of time in the range of about 0.75 to about 3 hours, before commencing said gradual reduction in temperature.

19. A process of claim 15 wherein, in b), the time period in which the temperature is gradually reduced is in the range of about 6 to about 16 hours.

20. A process of claim 15 wherein to effect the separation in c) liquid phase is drained away from said solids phase.

21. A process of claim 15 wherein in d) the solids phase is maintained under an inert atmosphere during at least a substantial portion of the time the temperature is being raised.

22. A process of claim 15 wherein in d) the temperature of the solids is gradually raised during a period of about 3 to about 5 hours.

23. A process of claim 15 wherein, before commencing said gradual reduction in temperature in b), the isomer mixture formed in a) is maintained at the nucleation temperature for a period of time sufficient for increasing the thickness of the crystal lattice being formed at said temperature; and wherein in b), the time period in which the temperature is gradually reduced is in the range of about 6 to about 16 hours.

24. A process of claim 15 wherein, before commencing said gradual reduction in temperature in b), the isomer mixture formed in a) is maintained at the nucleation temperature for a period of time sufficient for a crystal lattice to be formed; and wherein in b), the time period in which the temperature is gradually reduced is in the range of about 6 to about 16 hours.

25. A process of claim 15 wherein the isomer mixture formed in a) is maintained at the nucleation temperature for a period of time in the range of about 1 to about 3 hours, before commencing said gradual reduction in temperature; wherein in b), the time period in which the temperature is gradually reduced is in the range of about 6 to about 16 hours; wherein to effect the separation in c) liquid phase is drained away from said solids phase; and wherein in d) the temperature of the solids is gradually raised during a period of about 3 to about 5 hours.

26. A process of any of claims 15–25 wherein at least a portion of the additional liquid separated in e) is recycled to a) together with another charge of a mixture of toluenediamine isomers comprising at least 2,4-toluenediamine and 2,6-toluenediamine.

27. A process for separating 2,4-toluenediamine from a mixture of toluenediamine isomers comprising at least 2,4-toluenediamine, 2,6-toluenediamine, and optionally at least one other isomeric toluenediamine, and in which from about 79 to about 81 wt % of the mixture is 2,4-toluenediamine and from about 19 to about 21 wt % of the mixture is 2,6-toluenediamine, said method comprising:
  a) melting said mixture in a melt crystallizer, and then lowering the temperature of the mixture in the melt crystallizer to a nucleation temperature of 90±2°;
  b) maintaining the mixture in the melt crystallizer at said nucleation temperature for a period in the range of about 0.25 to about 3 hours;
  c) during a period in the range of about 12 to about 16 hours, gradually reducing the temperature of the mixture in the melt crystallizer from the nucleation temperature in b) to a temperature in the range of about 60 to about 70° C. such that the mixture is in the form of a solids phase enriched in 2,4-toluenediamine, and a liquid phase enriched in 2,6-toluenediamine;
  d) draining the liquid phase from the melt crystallizer while maintaining the temperature of the contents thereof in the range of about 60 to about 70° C.;
  e) maintaining the solids phase under an inert atmosphere in the melt crystallizer while gradually raising the temperature of the solids during a period in the range of about 5 to about 8 hours to a temperature in the range of about 100 to about 106° C., such that additional liquid is formed, and separating this liquid from the melt crystallizer such that solids further enriched in 2,4-toluenediamine remain in the melt crystallizer; and
  f) melting the solids remaining in the melt crystallizer, and draining such melted product from the melt crystallizer.

28. A process of claim 27 wherein said liquid phase drained from the melt crystallizer in d) is recycled to a) together with another charge of a mixture comprising at least 2,4-toluenediamine, 2,6-toluenediamine, and optionally at least one other isomeric toluenediamine.

29. A process of claim 27 wherein the mixture in b) is maintained in the melt crystallizer at said nucleation temperature for a period in the range of about 0.75 to about 3 hours.

* * * * *